(12) United States Patent
Linton et al.

(10) Patent No.: US 10,028,701 B2
(45) Date of Patent: Jul. 24, 2018

(54) DISPOSABLE INSERT HAVING SENSOR AND RFID

(71) Applicant: Attends Healthcare Products, Inc., Greenville, NC (US)

(72) Inventors: Steven D. Linton, Snellville, GA (US); Kevin Koski, Half Moon Bay, CA (US)

(73) Assignee: ATTENDS HEALTHCARE PRODUCTS, INC., Greenville, NC (US)

( * ) Notice: Subject to any disclaimer, the term of this patent is extended or adjusted under 35 U.S.C. 154(b) by 56 days.

(21) Appl. No.: 14/816,714

(22) Filed: Aug. 3, 2015

(65) Prior Publication Data

US 2016/0120473 A1 May 5, 2016

Related U.S. Application Data

(60) Provisional application No. 62/074,377, filed on Nov. 3, 2014.

(51) Int. Cl.
*G08B 23/00* (2006.01)
*A61B 5/00* (2006.01)
*A61F 13/49* (2006.01)
*A61F 13/42* (2006.01)
(Continued)

(52) U.S. Cl.
CPC ........ *A61B 5/6808* (2013.01); *A61B 5/14507* (2013.01); *A61B 5/208* (2013.01); *A61B 5/746* (2013.01); *A61F 13/42* (2013.01); *A61F 13/49* (2013.01); *A61B 5/0024* (2013.01); *A61B 5/14532* (2013.01); *A61B 5/14539* (2013.01); *A61B 5/14542* (2013.01);
(Continued)

(58) Field of Classification Search
CPC ... A61B 5/6808; A61B 5/14507; A61B 5/208; A61B 5/746; A61B 13/42; A61B 13/49
USPC ....................................................... 340/573.5
See application file for complete search history.

(56) References Cited

U.S. PATENT DOCUMENTS

| 6,093,869 A | 7/2000 | Roe et al. |
| 6,617,488 B1 * | 9/2003 | Springer ................. A61F 13/42 |
| | | 604/360 |
| 6,713,660 B1 | 3/2004 | Roe et al. |

(Continued)

FOREIGN PATENT DOCUMENTS

| WO | WO-2000000233 A1 | 1/2000 |
| WO | WO-2004060229 A2 | 7/2004 |

(Continued)

*Primary Examiner* — Eric M Blount
(74) *Attorney, Agent, or Firm* — Norton Rose Fulbright US LLP

(57) ABSTRACT

A diagnostic sheet for use in conjunction with a disposable absorbent garment is disclosed. The diagnostic sheet may be operable to wick fluid vertically, and includes one or more diagnostic elements and a radio frequency identification device (RFID). The one or more diagnostic elements may be integrated with the diagnostic sheet and positioned at a first region of the diagnostic sheet, and the RFID may be integrated with the diagnostic sheet and positioned proximate the first region. In the presence of the fluid, each of the one or more diagnostic elements may be configured to indicate a result of a particular diagnostic test. In the presence of the fluid, the RFID may be configured to provide an indication that the fluid wicked by the diagnostic sheet has reached the one or more diagnostic elements.

17 Claims, 6 Drawing Sheets

(51) Int. Cl.
*A61B 5/145* (2006.01)
*A61B 5/20* (2006.01)

(52) U.S. Cl.
CPC ............ *A61B 5/14546* (2013.01); *A61B 5/20* (2013.01); *A61B 5/201* (2013.01)

(56) References Cited

U.S. PATENT DOCUMENTS

| | | | |
|---|---|---|---|
| 7,002,054 B2 | 2/2006 | Allen et al. | |
| 7,365,238 B2 | 4/2008 | Diehl et al. | |
| 7,494,483 B2 | 2/2009 | Beck et al. | |
| 7,670,324 B2 | 3/2010 | LaVon et al. | |
| 7,755,488 B2 | 7/2010 | Dvorsky | |
| 7,838,721 B2 * | 11/2010 | Chen | A61F 13/15203 604/367 |
| 7,962,088 B2 | 7/2011 | Roe et al. | |
| 7,977,529 B2 | 7/2011 | Bergman et al. | |
| 8,187,241 B2 | 5/2012 | Lavon et al. | |
| 8,192,415 B2 | 6/2012 | LaVon et al. | |
| 8,217,217 B2 | 7/2012 | Diehl et al. | |
| 8,273,939 B2 | 9/2012 | Klofta et al. | |
| 8,586,820 B2 | 11/2013 | Hansson et al. | |
| 8,628,506 B2 | 1/2014 | Ales, III et al. | |
| 8,663,106 B2 | 3/2014 | Stivoric et al. | |
| 8,698,641 B2 | 4/2014 | Abraham et al. | |
| 8,987,543 B1 * | 3/2015 | Watson | A61B 5/208 604/361 |
| 2003/0158530 A1 | 8/2003 | Diehl et al. | |
| 2003/0199844 A1 | 10/2003 | LaVon et al. | |
| 2006/0069362 A1 | 3/2006 | Odorzynski et al. | |
| 2006/0224135 A1 | 10/2006 | LaVon et al. | |
| 2006/0253093 A1 | 11/2006 | Beck et al. | |
| 2007/0270774 A1 * | 11/2007 | Bergman | A61F 13/42 604/361 |
| 2008/0219885 A1 | 9/2008 | Horstman | |
| 2008/0266117 A1 | 10/2008 | Song et al. | |
| 2008/0269707 A1 * | 10/2008 | Song | A61F 13/42 604/385.01 |
| 2008/0274014 A1 | 11/2008 | Jumonville et al. | |
| 2009/0157023 A1 | 6/2009 | Song et al. | |
| 2009/0157024 A1 | 6/2009 | Song | |
| 2009/0157025 A1 | 6/2009 | Song et al. | |
| 2009/0315720 A1 * | 12/2009 | Clement | A61F 13/42 340/573.5 |
| 2010/0100008 A1 * | 4/2010 | Chciuk | A61F 13/42 600/584 |
| 2010/0114047 A1 | 5/2010 | Song et al. | |
| 2010/0145294 A1 | 6/2010 | Song et al. | |
| 2010/0159611 A1 | 6/2010 | Song et al. | |
| 2010/0290948 A1 | 11/2010 | Song | |
| 2011/0015599 A1 | 1/2011 | Song et al. | |
| 2012/0042722 A1 | 2/2012 | Song et al. | |
| 2012/0046628 A1 | 2/2012 | Wei et al. | |
| 2012/0109092 A1 * | 5/2012 | Austin | A61F 13/505 604/385.03 |
| 2012/0130268 A1 | 5/2012 | Fayed | |
| 2012/0130330 A1 | 5/2012 | Wilson et al. | |
| 2012/0143159 A1 | 6/2012 | Wei et al. | |
| 2013/0076509 A1 | 3/2013 | Ahn | |
| 2013/0303867 A1 | 11/2013 | Elfstrom et al. | |
| 2013/0307570 A1 | 11/2013 | Bosaeus et al. | |
| 2014/0014716 A1 | 1/2014 | Joyce et al. | |
| 2014/0015644 A1 | 1/2014 | Amann et al. | |
| 2014/0015645 A1 | 1/2014 | Striemer et al. | |
| 2014/0022058 A1 | 1/2014 | Striemer et al. | |
| 2014/0051951 A1 | 2/2014 | Kim | |
| 2014/0121487 A1 * | 5/2014 | Faybishenko | A61B 5/157 600/365 |

FOREIGN PATENT DOCUMENTS

| | | |
|---|---|---|
| WO | WO-2008012752 A2 | 1/2008 |
| WO | WO-2008012752 A3 | 4/2008 |
| WO | WO-2010070479 A2 | 6/2010 |
| WO | WO-2011007290 A2 | 1/2011 |
| WO | WO-2012023070 A2 | 2/2012 |
| WO | WO-2012073132 A1 | 6/2012 |
| WO | WO-2014043429 A1 | 3/2014 |
| WO | WO-2014043445 A2 | 3/2014 |
| WO | WO-2014043472 A1 | 3/2014 |
| WO | WO-2014054823 A2 | 4/2014 |

* cited by examiner

DISPOSABLE INSERT HAVING SENSOR AND RFID

CROSS-REFERENCE TO RELATED APPLICATIONS

The present application claims priority to co-pending U.S. Provisional Patent Application No. 62/074,377, entitled "DISPOSABLE INSERT HAVING SENSOR AND RFID," filed Nov. 3, 2014, the disclosure of which is hereby incorporated herein by reference.

TECHNICAL FIELD

The present disclosure is generally related to disposable absorbent garments. More particularly, the present disclosure is related to a diagnostic sheet for use in conjunction with a disposable absorbent garment to diagnose one or more conditions of a wearer of the disposable absorbent garment.

BACKGROUND

Use of disposable absorbent garments has become widespread. For example, infants and toddlers frequently wear disposable absorbent garments, such as diapers or training pants, until they are potty trained. Additionally, some adults utilize disposable absorbent garments, such as adult incontinence products. A disposable absorbent garment is designed to be worn around the waist and crotch area of the wearer. When the wearer insults the disposable absorbent garment, the bodily waste is retained within the disposable absorbent garment, and, subsequently, the disposable absorbent garment may be changed and discarded by appropriate means.

BRIEF SUMMARY

Systems, methods, computer-readable storage media, and apparatuses for generating alerts and notifications in response to detecting that a disposable absorbent garment has been insulted are disclosed herein. The alerts and notification may indicate that one or more diagnostic tests have been performed using one or more diagnostic elements integrated with a diagnostic sheet that is inserted into or integrated with the disposable absorbent garment. The one or more diagnostic elements may provide an indication of a result for each of the one or more diagnostic tests. The systems, methods, computer-readable storage media, and apparatuses may facilitate capturing of data (e.g., image data) representative of the results of each of the one or more diagnostic tests, and may provide the data to a healthcare provider for purposes of monitoring and/or diagnosing a condition of a wearer of disposable absorbent garments.

The foregoing has outlined rather broadly the features and technical advantages of the present disclosure in order that the detailed description that follows may be better understood. Additional features and advantages of the disclosure will be described hereinafter which form the subject of the claims. It should be appreciated by those skilled in the art that the specific embodiments disclosed herein may be readily utilized as a basis for modifying or designing other structures for carrying out the same purposes of the present disclosure. It should also be realized by those skilled in the art that such equivalent constructions do not depart from the scope of the present disclosure as set forth in the appended claims. The novel features which are believed to be characteristic of the present disclosure, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure.

BRIEF DESCRIPTION OF THE DRAWINGS

For a more complete understanding of the present disclosure, reference is now made to the following descriptions taken in conjunction with the accompanying drawing, in which.

DETAILED DESCRIPTION

Figure 1:
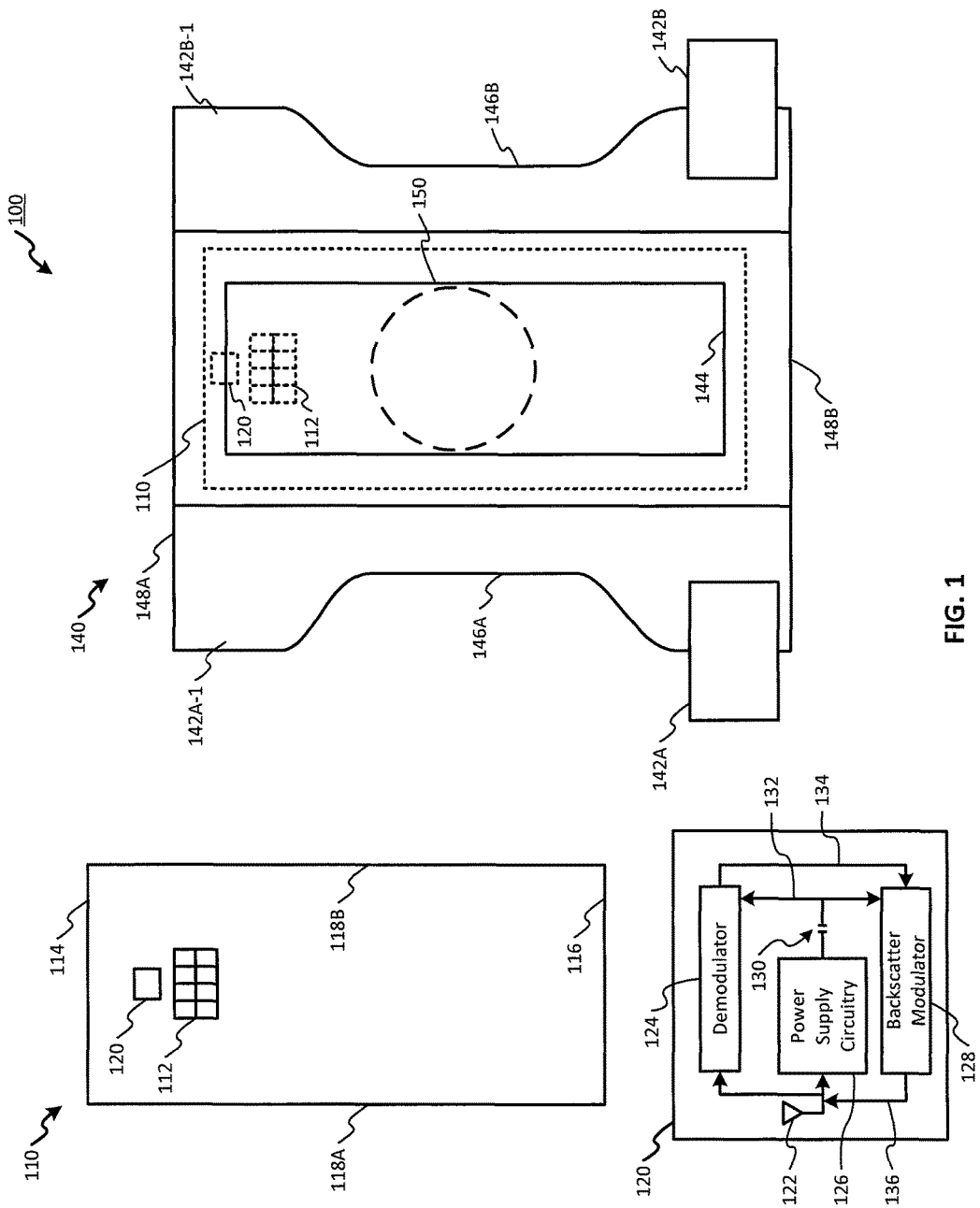
FIG. 1 is a block diagram of an illustrative embodiment of a diagnostic system for use with a disposable absorbent garment.

Referring to FIG. 1, a block diagram of an illustrative embodiment of a diagnostic system for use with a disposable absorbent garment is shown as a system 100. As shown in FIG. 1, the system 100 includes a diagnostic sheet 110 and a disposable absorbent garment 140. In an aspect, the disposable absorbent garment may be a diaper, training pants, and/or an adult incontinence product. The disposable absorbent garment 140 includes tabs 142A and 142B, an absorbable core 144, side edges 146A and 146B, a front longitudinal edge 148A, and a back longitudinal edge 148B.

The tabs 142A and 142B may be used to secure the disposable absorbent garment 140 around a waist and crotch of a wearer of the disposable absorbent garment 140. For example, during use, the front longitudinal edge 148A may rest between the wearer's crotch and belly button, and the back longitudinal edge 148B may rest above the wearer's buttocks and below the small of the wearer's back. Additionally, the side edges 146A and 146B may secure the disposable absorbent garment 140 around the wearer's upper thighs near the wearer's crotch. The tab 142A may be fastened to the front side of the disposable absorbent garment 140 proximate a region 142A-1, and the tab 142B may be fastened to the front side of the disposable absorbent garment 140 proximate a region 142B-1.

The disposable absorbent garment 140 may include a backsheet (not labeled in FIG. 1) that forms an outer surface of the disposable absorbent garment 140. The backsheet may be liquid impervious. The absorbent core 144 may be positioned on top of the backsheet. In an embodiment, the absorbent core 144 may include super absorbent polymer particles (SAP) intermixed with micro-fibrillated cellulose (MFC). In an additional or alternative embodiment, the absorbent core 144 may include SAPs, MFCs, tow, other absorbent materials, or a combination thereof configured to absorb fluids (e.g., urine) at a desired rate. A top sheet (not labeled in FIG. 1) may be positioned on top of the absorbent core 144. The top sheet may be formed from a liquid permeable material to allow liquids to pass through the top sheet to the absorbent core 144.

As shown in FIG. 1, the diagnostic sheet 110 includes one or more diagnostic elements 112, a radio frequency identification device (RFID) 120, a front edge 114, a back edge 116, and side edges 118A and 118B. In an aspect, the diagnostic sheet 110 may be formed from a nonwoven material, and may be configured as a fluid handling layer operable to wick fluid vertically. The diagnostic sheet 110 may have a hydrophilic, non-woven structure, and may be formed using natural or synthetic materials.

The one or more diagnostic elements 112 may be integrated with the diagnostic sheet 110 and may be positioned at a first region of the diagnostic sheet 110. For example, in FIG. 1, the first region is proximate the front edge 114 and is centered between edges 118A and 118B. During use, the front edge 114 of the diagnostic sheet 110 may be placed proximate the front longitudinal edge 148A of the disposable absorbent garment 140, as shown in the right side of FIG. 1. In additional or alternative embodiments, the one or more diagnostic elements may be positioned at a different location on the diagnostic sheet 110, such as a second region of the diagnostic sheet 110 proximate the back edge 116, or another location between the front edge 114 and the back edge 116. Additionally, it is noted that the positioning of the one or more diagnostic elements 112 and the RFID 120 may be altered by altering the orientation of the diagnostic sheet 110 relative to the disposable absorbent garment 140. For example, by rotating an orientation of the diagnostic sheet 180 degrees relative to the orientation shown in FIG. 1, the one or more diagnostic elements 112 and the RFID 120 may be positioned proximate the back longitudinal edge 148B of the disposable absorbent garment 140. The positioning of the one or more diagnostic elements 112 and the RFID 120 near the front edge 114 and/or the back edge 116 may make the diagnostic sheet 110, or a disposable absorbent garment that incorporates the diagnostic sheet 110 more attractive to consumers. For example, a consumer may be hesitant to use the diagnostic sheet 110 if the one or more diagnostic elements 112 and the RFID 120 are positioned in the center of the diagnostic sheet 110 as the consumers may be hesitant to place transmitters and diagnostic elements in close proximity to a crotch region of the wearer of the disposable absorbent garment 140.

The RFID 120 may be integrated with the diagnostic sheet 110 and may be positioned proximate the first region of the diagnostic sheet 110. The RFID 120 may be integrated with the diagnostic sheet 110 using any technique. For example, a manufacturer of the diagnostic sheet 110 may purchase RFIDs and attach the RFIDs to the diagnostic sheet 110 using an adhesive or other technique. As another example, the RFID may be printed on the diagnostic sheet 110 using a direct-write technique (e.g., a jetted atomized deposition (JAD) technique that allows metal or a polymer to be placed on a structure in a manner similar to an ink jet printer). As shown in FIG. 1, the RFID 120 is positioned between the first region (e.g., the location of the one or more diagnostic elements 112) and the front edge 114 of the diagnostic sheet 110. In additional or alternative embodiments, the RFID 120 may be positioned proximate to the one or more diagnostic elements 112 in a lateral direction (e.g., between the one or more diagnostic elements 112 and the side edge 118A, or between the one or more diagnostic elements 112 and the side edge 118B). Additionally or alternatively, the RFID 120 may be positioned proximate the back edge 116 (e.g., when the one or more diagnostic elements are positioned at the second region of the diagnostic sheet 110 proximate the back edge 116). Additional aspects of the RFID 120 are described in detail below.

The diagnostic sheet may 110 be configured for use in conjunction with the disposable absorbent garment 140 to facilitate diagnostic testing of a condition of the wearer of the disposable absorbent garment 140. For example, as shown in the right side of FIG. 1, the diagnostic sheet 110 may be configured to be positioned on top of the absorbable core 144 of disposable absorbent garment 140. In an embodiment, the diagnostic sheet 110 may be integrated with the disposable absorbent garment 140. For example, the diagnostic sheet 110 may serve as a top sheet of the disposable absorbent garment 140, and may be integrated into the disposable absorbent garment 140 during a manufacturing process. In an additional or alternative embodiment, the diagnostic sheet 110 may be inserted into the disposable absorbent garment 140 after the disposable absorbable garment 140 has been manufactured. For example, a diagnostic sheet 110 may be placed on top of a top sheet of a manufactured disposable absorbent garment 140 prior to packaging the disposable absorbent garment 140 for sale and/or distribution. In this embodiment, the diagnostic sheet 110 may be place over an intermediate top sheet (e.g., a top sheet of the manufactured disposable absorbent garment 140) and the diagnostic sheet 110 may be removed if the user does not desire to use it. If removed, the disposable absorbable garment 140 may still be used as it normally would. In yet another additional or alternative embodiment, the diagnostic sheet 110 may be manufactured, packaged, and sold/distributed separate from the disposable absorbent garment 140. A consumer may purchase the diagnostic sheet 110 (or a package of diagnostic sheets) as an add-on for use in conjunction with any brand, style, make, etc. of disposable absorbent garment 140, such as for assisting with the monitoring and/or diagnostic testing of a condition of a wearer of the disposable absorbent garment 140. In an aspect, the diagnostic sheet 110 may include an adhesive strip or other mechanism (not shown in FIG. 1) for securing the diagnostic sheet 110 to the disposable absorbent garment 140. In still another additional or alternative embodiment, the disposable absorbent garment 140 may have a pocket and the diagnostic sheet 110 may be inserted into the pocket. For example, the diagnostic sheet 110 may be formed as a small insert sized to fit within the pocket. The pocket may include a window that allows for easy viewing of the one or more diagnostic elements 112 when the diagnostic sheet 110 is inserted into the pocket. In an embodiment, the window may be formed using a plastic covering. In an additional or alternative embodiment, the window may simply be an opening in the pocket.

During operation, the wearer of the disposable absorbable garment 140 may insult the disposable absorbent garment 140 proximate an insult area 150 (e.g., a crotch area of the disposable absorbent garment 140). When the disposable absorbent garment is insulted, the diagnostic sheet 110 may be exposed to fluid (e.g., urine) and may begin to wick the fluid vertically towards the one or more diagnostic elements 112 and the RFID 120. As the fluid reaches one or more diagnostic elements 112, one or more diagnostic tests may be initiated. For example, when the fluid reaches and begins to interact with the one or more diagnostic elements 112, each the one or more diagnostic elements 112 may react with the fluid to provide an indication of a particular diagnostic test (e.g., an indication of a results of a particular urinalysis test). Stated another way, each of the one or more diagnostic elements 112 may be configured to indicate a result of a particular diagnostic test in the presence of the fluid wicked to one or more diagnostic elements 112 by the diagnostic sheet 110. The one or more diagnostic elements 112 may take a varying number of minutes to effectively react with the fluid to provide an accurate reading. Additionally, overexposure to the fluid may cause the one or more diagnostic elements 112 to provide a false positive reading due to oversaturation by the fluid. Thus, the timing between the fluid reaching the one or more diagnostic elements 112 and checking (e.g., by the wearer of the disposable absorbable garment 140 or a caregiver of the wearer) of the one or more diagnostic elements 112 to obtain the indications of the one or more diagnostic tests is of importance.

The RFID 120 may be configured to provide an indication that the fluid wicked by the diagnostic sheet 110 has reached the one or more diagnostic elements 112 when the RFID 120 is in the presence of the fluid wicked by the diagnostic sheet 110. To illustrate, as shown in FIG. 1, the RFID 120 includes an antenna 122, a demodulator 124, a power supply circuitry 126, and a backscatter modulator 128. The power supply circuitry 126 may be configured to power the RFID 120 in response to receiving a wireless signal from an interrogator device (not shown in FIG. 1) at the antenna 122. As shown in FIG. 1, the antenna 122 may provide an input (e.g., the wireless signal received from the interrogator device) to the demodulator 124 and the power supply circuitry 126, and may receive an output (e.g., a backscatter signal) generated by the backscatter modulator 128.

The power supply circuitry 126 may include a radio frequency-to-direct current (RF-DC) rectifier configured to power the demodulator 124 and the backscatter modulator 128 in response to receiving the input (e.g., the wireless signal) from the antenna 122. The power supply circuitry 126 may power to the demodulator 124 and the backscatter modulator 128 via power traces 132. As shown in FIG. 1, the power traces 132 may include a gap 130. The gap 130 may be configured to prevent the power supply circuitry 126 from providing power to the demodulator 124 and the backscatter modulator 128 until at least a portion of the RFID 120 (e.g., a portion including the gap 130) is in the presence of the fluid wicked to the RFID 120 by the diagnostic sheet 110. For example, urine has approximately 9/10 saline content. Thus, when the gap 130 is in the presence of the fluid (e.g., urine), the power generated by the power supply circuitry 126 may be allowed to pass through the gap 130 (e.g., the saline in the fluid may conduct the power across the gap) and be provided to the demodulator 124 and the backscatter modulator 128. When powered, the input received at the demodulator 124 may be demodulated to produce a demodulated signal, and the demodulated signal may be provided to the backscatter modulator 128 via a data trace 134.

The backscatter modulator 128 may generate a backscatter signal based on the received signal, and may provide the backscatter signal to the antenna 122 for transmission. The indication that the disposable absorbent garment 140 has been insulted may be provided via the backscatter signal. For example, the backscatter modulator 128 may receive the demodulated signal, and to generate the backscatter signal based on the demodulated signal. The backscatter modulator 128 may generate the backscatter signal by modulating the demodulated signal received from the demodulator. The backscatter signal may be provided to the antenna 122 for transmission via an output trace 136. In response to receiving the backscatter signal, the antenna 122 may transmit the backscatter signal, which may subsequently be detected by the interrogator device (not shown in FIG. 1). In response to detecting the backscatter signal from the RFID 120, the interrogator device may be configured to generate an alert to indicate that the disposable absorbent garment 140 has been insulted, as described in more detail below. It is noted that the particular components (e.g., the antenna 122, the demodulator 124, the power supply circuitry 126, and the backscatter modulator 128) described in connection with the configuration of the RFID 120 are provided by way of illustration, rather than limitation, and other configurations of the RFID 120 may be used to generate and provide a signal to the interrogator device. For example, in an additional or alternative embodiment of a passive RFID that may be used in conjunction with the diagnostic sheet 110 is described with reference to FIG. 3. In another additional or alternative embodiment, the RFID 120 may be an active RFID device.

The positioning of the RFID 120 between the one or more diagnostic elements 112 and the front edge 114 of the diagnostic sheet 110 may facilitate accurate timing, and therefore accurate results, of the diagnostic tests provided by the one or more diagnostic elements 112. For example, by positioning the RFID 120 above the one or more diagnostic elements 112 with respect to the front edge 114, the fluid will reach the one or more diagnostic elements 112 before reaching the RFID 120. Thus, it will take longer for the fluid to be wicked vertically to the RFID 120, thereby providing a time window during which the one or more diagnostic elements 112 are allowed to interact with the fluid to provide the indicators representative of the results of the one or more diagnostic tests prior to the RFID 120 providing the indication (e.g., the backscatter signal) that the disposable absorbent garment 140 has been insulted. In an embodiment, the positioning and the spacing of the one or more diagnostic elements 112 and a wicking rate of the diagnostic sheet 110 may also be used to configure a duration of the time window. For example, diagnostic elements associated with diagnostic tests that require a longer exposure to the fluid to provide an accurate test result may be positioned lower (e.g., closer to the insult area 150) on the diagnostic sheet 110 relative to other diagnostic elements associated with other diagnostic tests that require less exposure to the fluid to provide an accurate test result. The locations and the spacing of each of the one or more diagnostic elements 112 may be determined based, at least in part, on the wicking rate of the diagnostic sheet 110.

In an additional or alternative embodiment, the positioning of the RFID 120 may be used to configure the time window. For example, after the disposable absorbent garment 140 is insulted, it may take a variable amount of time before the disposable absorbent garment 140 is changed. Factors that may influence the amount of time may include the time of day when the disposable absorbent garment 140 is insulted (e.g., at night when the wearer and/or a caregiver are sleeping vs. during the daytime when the wearer and/or the caregiver are awake), the age of the wearer (e.g., older wearers are more likely to be able to communicate with a caregiver to indicate that the disposable absorbent garment 140 has been insulted), a location of the wearer (e.g., it may take less time to change the disposable absorbent garment 140 at a residence where a family member is likely to be on hand at all times and may have less persons to care for than a hospital, assisted living facility, or daycare facility), etc. The distance between one or more diagnostic elements 112 and the RFID 120 may be configured to provide the indication after an average time period required to ensure that all of the one or more diagnostic elements 112 have been in the presence of the fluid a sufficient amount of time to provide an accurate indication for each of the corresponding one or more diagnostic tests, but prior to the one or more diagnostic elements 112 reaching a saturation point (e.g., a point where overexposure to the fluid may cause a false positive test result). In an embodiment, the RFID 120 may positioned at a distance from the one or more diagnostic elements 112 such that the indication is provided after at least a minimum exposure time (e.g., 2 minutes) has elapsed and before a maximum exposure time (e.g., 2 hours) has elapsed, where the exposure time is a relative an amount of time during which the one or more diagnostic elements 112 are exposed to the fluid. In an embodiment, the one or more diagnostic elements 112 may include an element that is configured to provide an indication that the other diagnostic elements have been over exposed (e.g., reached a saturation point). For example, one of the one or more diagnostic elements 112 may be enclosed by a gel or other substance that dissolves in the presence of liquids, such as the fluid. The thickness of the gel or another property may be used to configure the diagnostic element to not interact with the fluid unless a sufficient amount of time has elapsed to indicate that the other diagnostic elements have been over exposed to the fluid and may be providing a false positive test result.

Disposable absorbent garments come in a variety of shapes. Therefore, a single size diagnostic sheet 110 may not be suitable for all sizes of disposable absorbent garments. For example, a diagnostic sheet 110 sized for an adult incontinence product may not be suitable for use with a disposable absorbent garment designed for a newborn or toddler. In an embodiment, the diagnostic sheet 110 may include one or more perforations for resizing the diagnostic sheet 110. The one or more perforations may extend across a width (e.g., from the side edge 118A to the side edge 118B) of the diagnostic sheet 110 for resizing a length of the diagnostic sheet 110, and/or may extend across a length (e.g., from the front edge 114 to the back edge 116) of the diagnostic sheet 110 for resizing a width of the diagnostic sheet 110. When the diagnostic sheet 110 includes perforations for resizing the width and/or length of the diagnostic sheet 110, the perforations may be located such that the one or more perforations do not pass through the one or more diagnostic elements 112 and the RFID 120.

Each of the one or more diagnostic elements 112 may be configured to indicate, when in the presence of the fluid, a result of a particular urinalysis diagnostic test. Exemplary urinalysis diagnostic tests may include a pH test, a specific gravity test, a protein test, a blood test, a glucose test, a ketone test, a bilirubin test, a urobilinogen test, a nitrites test, and a leukocytes test. Each of the different urinalysis diagnostic tests may provide an indication of a particular condition of the wearer of the disposable absorbent garment 140. For example, a result of the specific gravity test may indicate whether the wearer of the disposable absorbent garment 140 is dehydrated, while a result of the glucose test may provide an indication that the wearer of the disposable absorbent garment 140 may have diabetes. As yet another example, a result of the nitrites test may indicate whether the wearer of the disposable absorbent garment 140 has a urinary tract infection. The exemplary tests disclosed herein are provided by way of illustration, rather than by way of limitation, and other urinalysis diagnostic tests may be incorporated into the one or more diagnostic elements 112.

The indication (e.g., the backscatter signal) provided by the RFID 120 may be detected or received by the interrogator device and the interrogator device may alert a caregiver. The alert may indicate to the caregiver that the disposable absorbent garment 140 has been insulted, and the caregiver may subsequently change the disposable absorbent garment. Illustrative aspects of generating alerts using the diagnostic sheet 110 and an interrogator device are described with reference to FIGS. 2-5. When the caregiver changes the disposable absorbent garment 140, the caregiver may view the one or more diagnostic elements 112 to obtain the results of the one or more diagnostic tests. Additionally or alternatively, the caregiver may capture an image of the one or more diagnostic elements 112, and therefore capture the results of the one or more diagnostic tests. The image may be subsequently provided to a healthcare provider (e.g., a doctor) who may use the results depicted in the image to diagnose or monitor a condition of the wearer of the disposable absorbent garment 140.

By providing notifications to a caregiver to indicate that the disposable absorbent garment 140 has been insulted, the system 100 may provide an improved method for monitoring and diagnosing a condition of a wearer of a disposable absorbent garment. Additionally, because the notifications are provided to the caregiver in a timely manner (e.g., before the one or more diagnostic elements have become saturated and are no longer providing accurate indications of results of one or more diagnostic tests), the monitoring and diagnosis of the condition of the wearer of the disposable absorbent garment 140 may be more accurate. This may improve the medical treatment and care that the wearer receives, and may help diagnose at least some conditions early, allowing the wearer to be treated for those conditions in the early stages and minimizing the negative impact of those conditions on the wearer. Thus, the system 100 may provide improvements in the healthcare and health monitoring fields. Additionally, because the images of the one or more diagnostic elements 112 may be provided to the medical or healthcare provider from any location (e.g., via e-mail, text message, uploading the image to a website, etc.), the system 100 may allow home health monitoring without requiring a doctor or medical professional to visit the residence of the wearer, thereby reducing the costs to provide some home health monitoring and treatment solutions. Furthermore, the system 100 may benefit users of wearable disposable garments who have difficulty communicating or who cannot communicate and require assistance with changing disposable absorbent garments.

Figure 2:
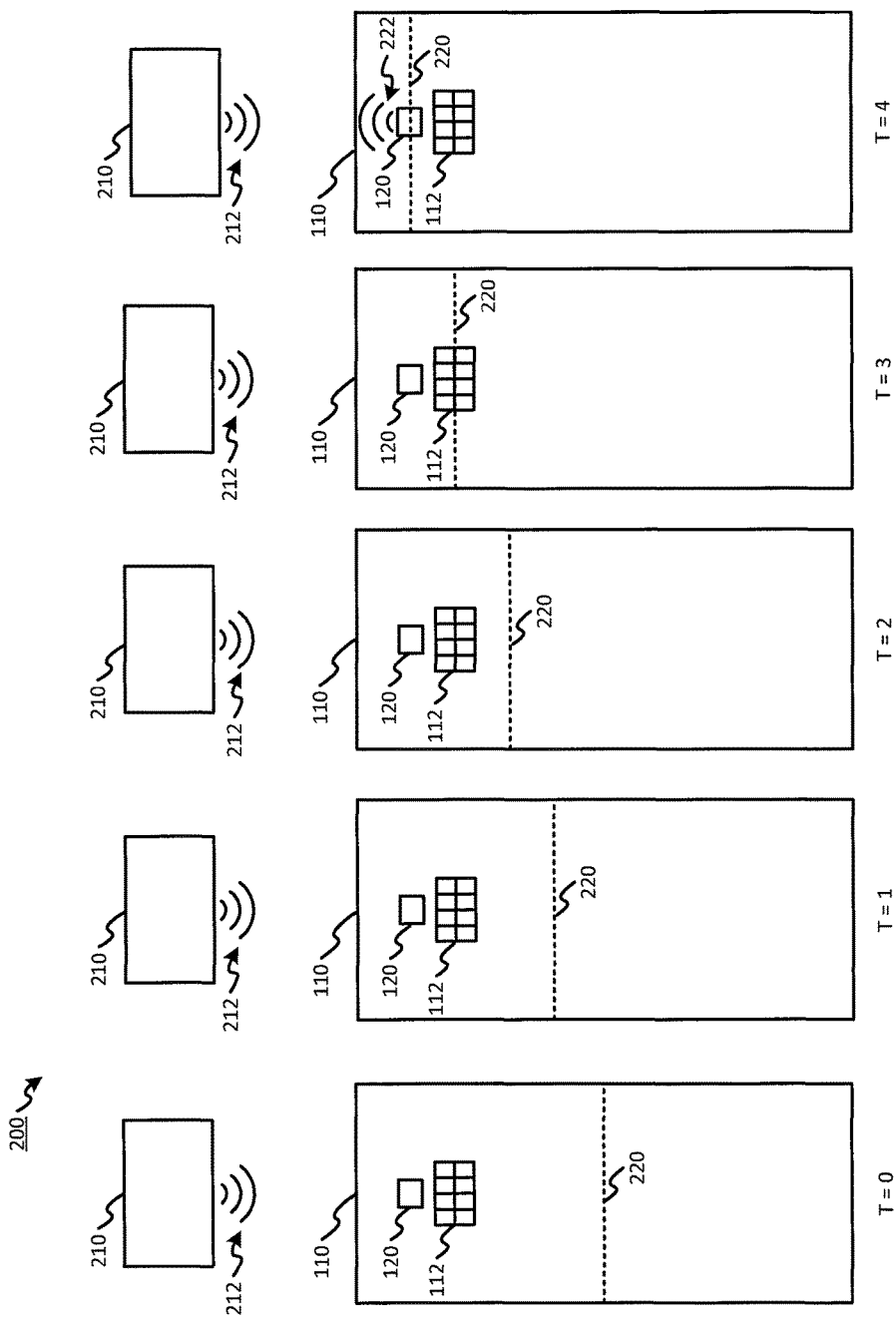
FIG. 2 is a block diagram of another illustrative embodiment of a diagnostic system for use with a disposable absorbent garment.

Referring to FIG. 2, a block diagram of another illustrative embodiment of a diagnostic system for use with a disposable absorbent garment is shown as a system 200. As shown in FIG. 2, the system 200 includes the diagnostic sheet 110 of FIG. 1 that includes the RFID 120 and the one or more diagnostic elements 112, and includes an interrogator device 210. The interrogator device 210 may be a wireless transceiver operable to transmit an interrogation signal 212, and to receive or detect wireless signals (e.g., a backscatter signal) generated by the RFID 120.

In FIG. 2, the RFID 120 is configured as a passive RFID device, as described with reference to FIG. 1, and may be configured to power the RFID 120 when a wireless signal (e.g., the interrogator signal 212) is received from the interrogator device 210 and at least a portion of RFID 120 (e.g., a portion including the gap 130) is in the presence of the fluid wicked to the RFID 120 by the diagnostic sheet 110.

To illustrate, assume that the diagnostic sheet has been inserted into or is integrated with a disposable absorbent garment (e.g., the disposable absorbent garment 140 of FIG. 1). At a first time (e.g., T=0), the disposable absorbent garment may be insulted. In FIG. 2, the dashed line 220 indicates a distance that fluid (e.g., urine) has been wicked by the diagnostic sheet 110. As can be seen in FIG. 2, after some time has passed (e.g., T=1 and T=2), the fluid has been wicked vertically but has not reached the one or more diagnostic elements 112.

At a second time (e.g., T=3), the fluid has been wicked vertically and has reached some, but not all of the one or more diagnostic elements 112. Thus, at the second time at least some of the one or more diagnostic elements 112 may be interacting with the fluid to generate an indication of a result of a particular diagnostic test. As shown in FIG. 2, the RFID 120 is not in the presence of the fluid during the time period starting from the first time (e.g., T=0) and ending at the second time (e.g., T=3), and, therefore, does not generate the backscatter signal.

At a third time (e.g., T=4), the fluid has been wicked vertically by the diagnostic sheet 110 and has reached all of the diagnostic elements 112. Additionally, at the third time, a portion of the RFID 120 (e.g., the portion including the gap 130 described with reference to FIG. 1) is in the presence of the fluid, causing the RFID 120 to generate a backscatter signal 222. The interrogator device 210 may receive or detect the backscatter signal 222, and may generate an alert to indicate that the disposable absorbent garment has been insulted and that the one or more diagnostic elements 112 are in the presence of the fluid. Additional illustrative aspects of alerts that may be generated by the interrogator device 210 are described with reference to FIGS. 4 and 5.

The system 200 illustrated in FIG. 2 may facilitate improved diagnostic testing of fluid introduced when a disposable absorbent garment is insulted. For example, as explained above, the RFID 120 does not generate the backscatter signal 222 until each of the one or more diagnostic elements 112 is in the presence of the fluid. Thus, when the backscatter signal 222 is generated by the RFID 120 and detected or received by the interrogator device 210, each of the one or more diagnostic elements 112 has initiated or completed interaction with the fluid to provide an indication of a result of a particular diagnostic test. Additionally, the alert generated by the interrogator device 210 may apprise a caregiver of the wearer of the disposable absorbent garment that the disposable absorbent garment has been insulted and/or that the one or more diagnostic elements 112 are currently (e.g., at the time the alert is generated) providing accurate results for the one or more diagnostic tests. The alert may cause the caregiver to attend to changing the disposable absorbent garment and viewing/capturing an image of the one or more diagnostic elements 112, thereby obtaining accurate results for the one or more diagnostic tests.

Figure 3:
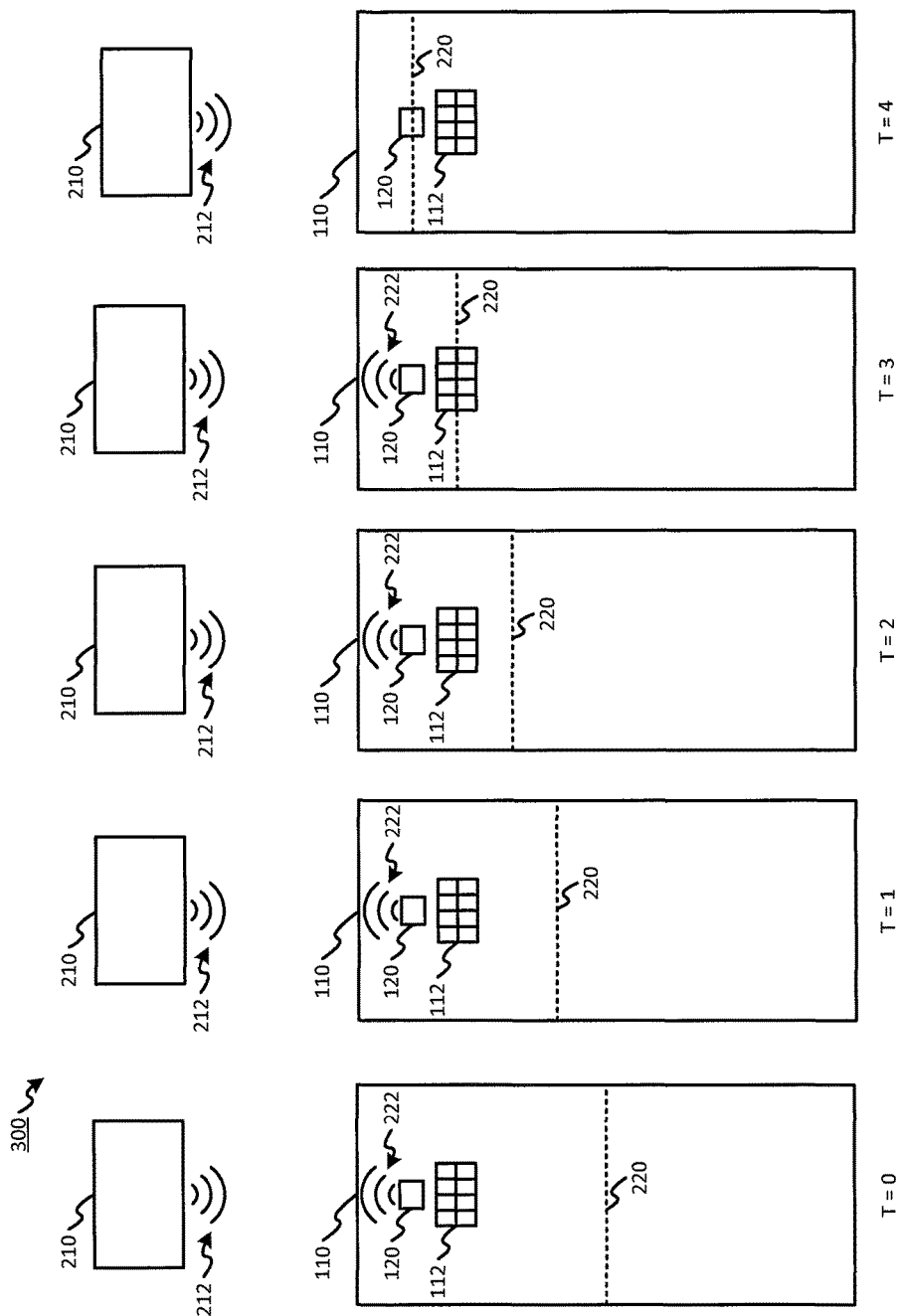
FIG. 3 is a block diagram of yet another illustrative embodiment of a diagnostic system for use with a disposable absorbent garment.

Referring to FIG. 3, a block diagram of yet another illustrative embodiment of a diagnostic system for use with a disposable absorbent garment is shown as a system 300. As shown in FIG. 2, the system 200 includes the diagnostic sheet 110 of FIG. 1 that includes the RFID 120 and the one or more diagnostic elements 112, and includes an interrogator device 210. The interrogator device 210 may be a wireless transceiver operable to transmit an interrogation signal 212, and to receive or detect wireless signals (e.g., a backscatter signal) generated by the RFID 120.

In FIG. 3, the RFID 120 is configured as a passive RFID device configured to power the RFID 120 when a wireless signal (e.g., the interrogator signal 212) is received from the interrogator device 210, and to cease providing power to the RFID 120 (e.g., cease providing power to the demodulator 124 and the backscatter modulator 128) when at least a portion of RFID 120 is in the presence of the fluid wicked to the RFID 120 by the diagnostic sheet 110. To illustrate, assume that the diagnostic sheet has been inserted into or is integrated with a disposable absorbent garment (e.g., the disposable absorbent garment 140 of FIG. 1). At a first time (e.g., T=0), the disposable absorbent garment may be insulted. In FIG. 3, the dashed line 220 indicates a distance that fluid (e.g., urine) has been wicked by the diagnostic sheet 110. As can be seen in FIG. 3, after some time has passed (e.g., T=1 and T=2), the fluid has been wicked vertically but has not reached the one or more diagnostic elements 112.

At a second time (e.g., T=3), the fluid has been wicked vertically and has reached some, but not all of the one or more diagnostic elements 112. Thus, at the second time at least some of the one or more diagnostic elements 112 may be interacting with the fluid to generate an indication of a result of a particular diagnostic test. As shown in FIG. 3, the RFID 120 is not in the presence of the fluid during the time period starting from the first time (e.g., T=0) and ending at the second time (e.g., T=3), and, therefore, generates a backscatter signal 222, that may be received or detected by the interrogator device 210. The interrogator device 210 may configured such that the presence of the backscatter signal 222 signifies that the disposable absorbent garment has not been insulted, and may not provide an alert.

At a third time (e.g., T=4), the fluid has been wicked vertically by the diagnostic sheet 110 and has reached all of the diagnostic elements 112. Additionally, at the third time, a portion of the RFID 120 is in the presence of the fluid, causing the RFID 120 to cease transmission of the backscatter signal 222. The interrogator device 210 may detect that the RFID 120 is not transmitting the backscatter signal 222, and may generate an alert to indicate that the disposable absorbent garment has been insulted and that the one or more diagnostic elements 112 are in the presence of the fluid. Additional illustrative aspects of alerts that may be generated by the interrogator device 210 are described with reference to FIGS. 4 and 5.

In an embodiment, the RFID 120 of FIG. 3 may include a gap (not shown in FIGS. 1-3) that causes a short in the power supply circuitry 126 when in the presence of the fluid wicked to the RFID 120. The short may prevent the power supply circuitry 126 from powering the demodulator 124 and/or the backscatter modulator 128. In an additional or alternative embodiment, the RFID 120 may include a normally closed switch (not shown in FIGS. 1-3) that enables the power generated by the power supply circuitry to be provided to the demodulator 124 and the backscatter modulator 128. The normally closed switch may be coupled to a trace including a gap (e.g., a gap similar to the gap 130) that, when in the presence of the fluid, causes the normally closed switch to open, thereby preventing the power supply circuitry from providing power to the demodulator 124 and the backscatter modulator 128. It is noted that the example configurations provided above are provided by way of illustration, rather than by way of limitation, and that other configurations of the RFID 120 may be utilized to cause the RFID 120 to cease providing a backscatter signal when in the presence of the fluid.

The system 300 illustrated in FIG. 3 may facilitate improved diagnostic testing of fluid introduced when a disposable absorbent garment is insulted. For example, as explained above, the RFID 120 ceases to generate the backscatter signal 222 when each of the one or more diagnostic elements 112 is in the presence of the fluid. Thus, when the backscatter signal 222 ceases to be detected or received by the interrogator device 210, each of the one or more diagnostic elements 112 has initiated or completed interaction with the fluid to provide an indication of a result of a particular diagnostic test. Additionally, the alert generated by the interrogator device 210 may apprise a caregiver of the wearer of the disposable absorbent garment that the disposable absorbent garment has been insulted and/or that the one or more diagnostic elements 112 are currently (e.g., at the time the alert is generated) providing accurate results for the one or more diagnostic tests. The alert may cause the caregiver to attend to changing the disposable absorbent garment and viewing/capturing an image of the one or more diagnostic elements 112, thereby obtaining accurate results for the one or more diagnostic tests.

Figure 4:
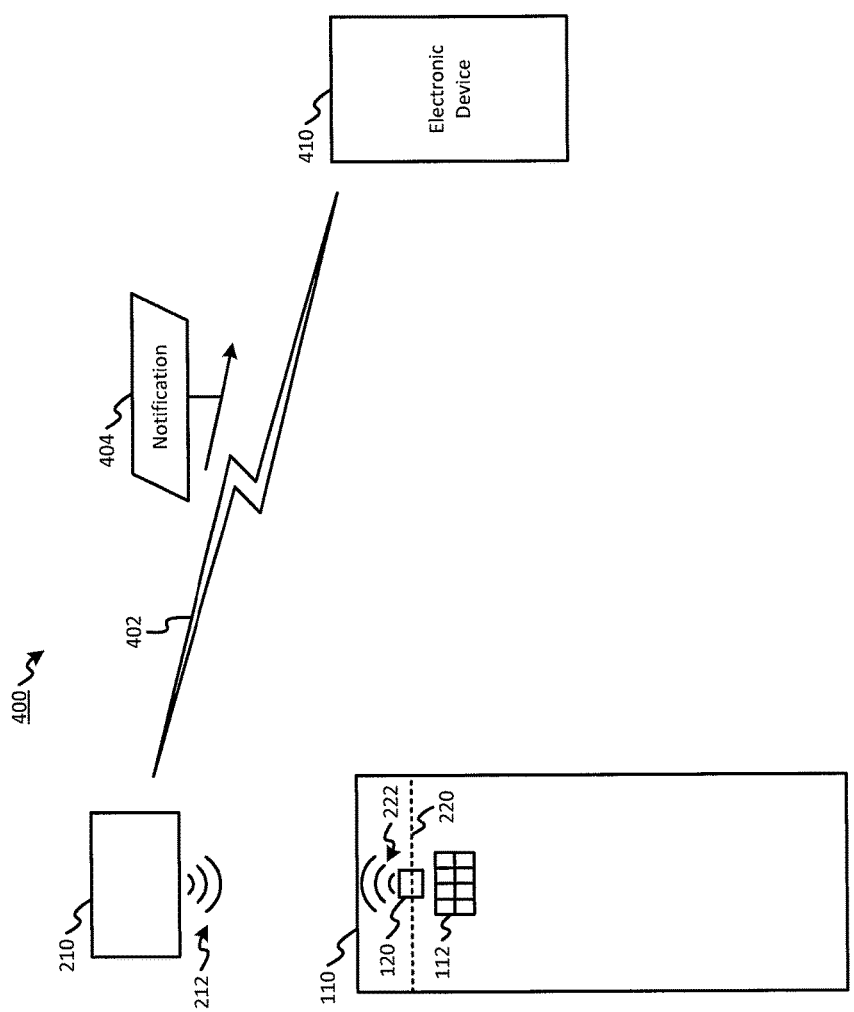
FIG. 4 is a block diagram of another illustrative embodiment of a system for providing alerts in response detecting that a disposable absorbent garment has been insulted.

Referring to FIG. 4, a block diagram of another illustrative embodiment of a system for providing alerts in response detecting that a disposable absorbent garment has been insulted is shown as a system 400. As shown in FIG. 4, the system 400 includes the diagnostic sheet 110 of FIG. 1 that includes the RFID 120 and the one or more diagnostic elements 112, the interrogator device 210 of FIGS. 2-3, and an electronic device 410. The electronic device 410 may be a personal computing device, a laptop computing device, a tablet computing device, a smartphone, a personal digital assistant (PDA), a wireless communication device, or any other electronic device operable to receive data via a network. For example, in FIG. 4, the electronic device 410 may receive data (e.g., the alert) from the interrogator device 210 via a wireless link 402.

In FIG. 4, the diagnostic sheet 110 is shown at the third time (e.g., T=4) of FIG. 2. Stated another way, in FIG. 4, the fluid has been wicked to the RFID 120, as indicated by the dashed line 220, and the RFID 120 is generating the backscatter signal 222 to provide an indication to the interrogator device 210 that the disposable absorbent garment has been insulted and that the one or more diagnostic elements 112 are in the presence of the fluid and are providing accurate results for the corresponding one or more diagnostic tests. In response to receiving or detecting the indication (e.g., the backscatter signal 222), the interrogator device 210 may generate an alert, shown in FIG. 4 as a notification 404, that indicates the fluid has been wicked to the one or more diagnostic elements 112 by the diagnostic sheet 110. The notification 404 may be provided to the electronic device 410 via the wireless link 402. In an embodiment, the notification 404 generated by the interrogator device 210 may be a text message, an automated voice messaging system message (e.g., a call to the electronic device 410 that, when answered by a user of the electronic device 410, plays an automated message indicating that the disposable absorbent garment has been insulted and/or needs to be changed), or some other alert mechanism provided to the electronic device 410. In an additional or alternative embodiment, the notification 404 may be an audible alert (e.g., the interrogator device 210 may generate an audible tone or sound to indicate that the disposable absorbent garment has been insulted and/or needs to be changed), a visual alert (e.g., the interrogator device 210 may generate an flashing light indicate that the disposable absorbent garment has been insulted and/or needs to be changed), or a combination of audible and visual alerts.

In yet another additional or alternative embodiment, the notification 404 may be provided to the electronic device 410 in combination with an audible and/or visual alert. This may be beneficial in situations where a parent wants to be apprised of how responsive a caregiver is when caring for the parent's child. For example, the caregiver may receive the audible and/or visual alerts, while the parent may receive an alert at his or her electronic device 410. The interrogator device 210 may include a reset button that may be pressed to stop the audible and/or visual alerts. For example, the caregiver may press the reset button when the caregiver changes the disposable absorbent garment. During the changing, the caregiver may capture an image (e.g., using a camera or other imaging device) of the one or more diagnostic elements 112 to preserve the results of the one or more diagnostic tests. In an embodiment, the interrogator device 210 may include an imaging device that may be used to capture the image of the one or more diagnostic elements 112 when the disposable absorbent garment is changed. Once the image is captured, the interrogator device 210 may provide the image to the electronic device 410 and/or to another electronic device, such as an electronic device associated with a healthcare provider, by including the image in a second notification. The healthcare provider may monitor a condition of the wearer of the disposable absorbent garment by analyzing the results of the one or more diagnostic tests, where the results are indicated by the image of the one or more diagnostic elements 112 captured when the disposable absorbent garment was changed. In an embodiment, the interrogator device 210 may be configured to generate an additional alert or notification to indicate that the one or more diagnostic elements 112 have been over exposed to the fluid and may not be providing accurate diagnostic test results. For example, if a threshold period of time (e.g., 2 hours) elapses between receiving the indication from the RFID 120 and receiving an input (e.g., pressing of the reset button) indicating that the disposable absorbent garment has been changed, the interrogator device 210 may generate additional alerts and/or notifications to signal to the caregiver that the results of the one or more diagnostic tests may be invalid.

Because the RFID 120 remains in the presence of the fluid, even after the disposable absorbent garment has been changed, the RFID 120 may continue to generate the backscatter signal. Thus, the interrogator device 210 may continue to detect and/or receive the backscatter signal 222. To prevent the interrogator device 210 from generating false notifications (e.g., generating a subsequent notification based on the RFID included in the changed disposable absorbent garment), the disposable absorbent garment and/or the diagnostic sheet 110, may be discarded in a metal waste basket that includes a lid. The metal waste basket may prevent the RFID 120 from receiving the interrogator signal and/or generating the backscatter signal 222. Additionally, the metal waste basket may prevent the interrogator device 210 from receiving the backscatter signal 222 if generated by the RFID 120.

In an additional or alternative embodiment, the RFID 120 may include a programmable memory (not shown in FIG. 4) configured to store information representative of the demodulated signal, and the backscatter modulator may be configured to generate the backscatter signal 222 based on the information stored in the programmable memory. The programmable memory may be coupled to a switch (e.g., a normally closed switch) that, when closed, allows the programmable memory to be programmed with the information representative of the demodulated signal, and that, when in the presence of the fluid, causes the switch to open, thereby preventing further programming of the programmable memory, and thereby preventing the RFID 120 from modifying the backscatter signal 222. The interrogator device 210 may be configured with a reset button (not shown in FIG. 4). When the reset button is pressed, the interrogator device 210 may modify the interrogator signal 212, which may alter the expected backscatter signal (e.g., because the backscatter signal is generated based on the demodulated interrogator signal). Thus, the interrogator device 210 may distinguish between prior backscatter signals that have been addressed by a caregiver (e.g., backscatter signals for which a notification has been previously provided to the caregiver), and a backscatter signal generated by an RFID device that has been recently insulted.

Although the notification 404 is shown in FIG. 4 as being provided by a wireless link established directly between the interrogator device 210 and the electronic device 410, the wireless link 402 may be facilitated by one or more intermediate networks (not shown in FIG. 4), which may include wired and/or wireless networks, and/or may be facilitated by one or more one or more intermediate wired or wireless connections. In an embodiment, the interrogator device 210 may be one of a plurality of interrogator devices, and each of the plurality of interrogator devices may be communicatively coupled to the electronic device 410 via a wired or wireless connection and/or one or more intermediate wired and/or wireless networks. For example, the plurality of interrogator devices may be installed throughout the rooms of a home and may be coupled to a home network for providing the notification 404 to the electronic device 410.

The system 400 illustrated in FIG. 4 may facilitate improved diagnostic testing of fluid introduced when a disposable absorbent garment is insulted. For example, as explained above, the RFID 120 does not generate the backscatter signal 222 until each of the one or more diagnostic elements 112 is in the presence of the fluid. Thus, when the backscatter signal 222 is generated by the RFID 120 and detected or received by the interrogator device 210, each of the one or more diagnostic elements 112 has initiated or completed interaction with the fluid to provide an indication of a result of a particular diagnostic test. Additionally, the notification 404 generated by the interrogator device 210 may apprise a caregiver of the wearer of the disposable absorbent garment that the disposable absorbent garment has been insulted and/or that the one or more diagnostic elements 112 are currently (e.g., at the time the alert is generated) providing accurate results for the one or more diagnostic tests. The alert may cause the caregiver to attend to changing the disposable absorbent garment and viewing/capturing an image of the one or more diagnostic elements 112, thereby obtaining accurate results for the one or more diagnostic tests.

Additionally, integrating an imaging device with the interrogator device 210 may provide a convenient way to capture and store images of the one or more diagnostic elements 112, and to distribute the images to parents, medical professionals, or other entities that may use the images to diagnose a condition of the wearer of the disposable absorbent garment. Further, by including a reset button on the interrogator device, parties of interest may be apprised of when the disposable absorbent garment has been changed, and/or an amount of time that has elapsed between the disposable absorbent garment being insulted and changed (e.g., based on the relative times when the notification of the insulting of the disposable absorbent garment and the subsequent notification sent when the reset button was pressed). As a further advantage of the system 400 of FIG. 4, when the RFID 120 includes the programmable memory, the interrogator device 210 may alter the interrogator signal to reduce a likelihood that the interrogator device 210 transmits a false notification (e.g., a notification generated in response to a backscatter signal generated by a diagnostic sheet that has been discarded).

Figure 5:
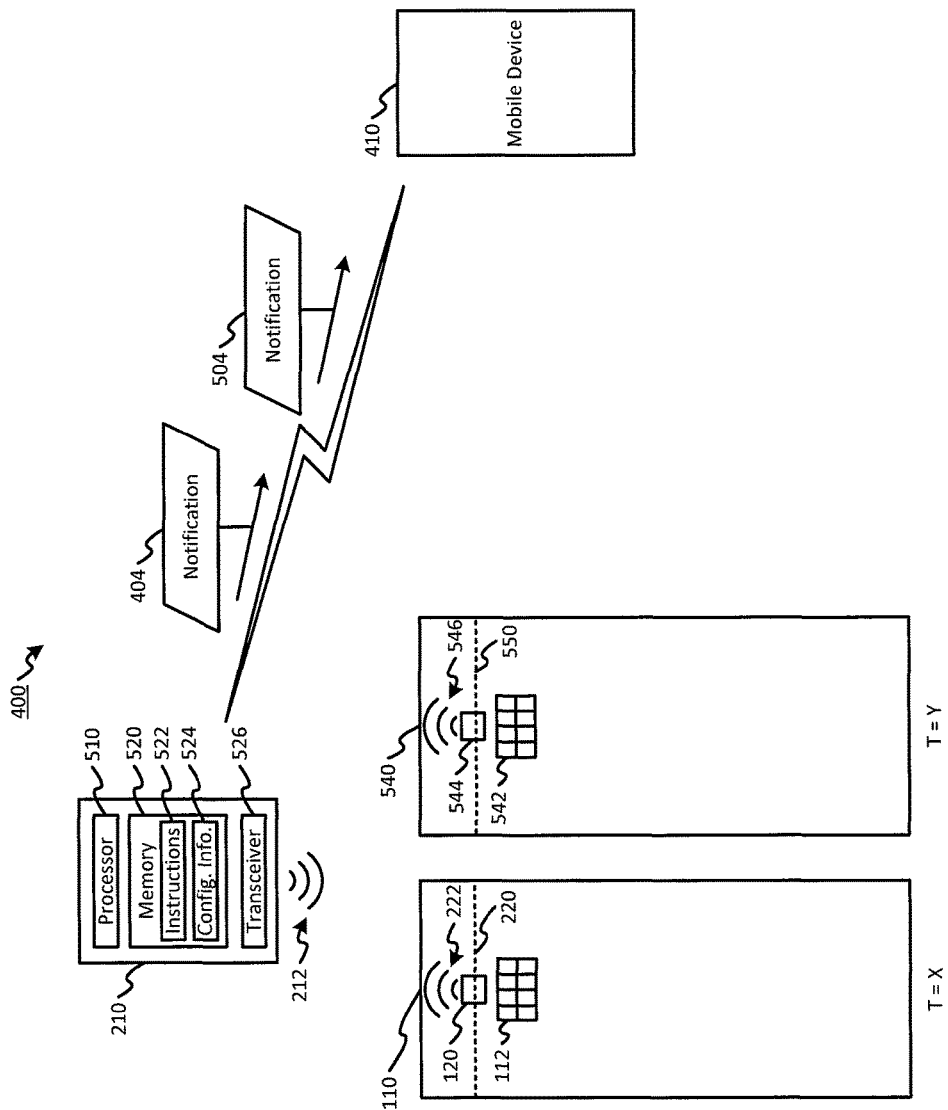
FIG. 5 is a block diagram of another illustrative embodiment of a system for providing alerts in response detecting that a disposable absorbent garment has been insulted.

Referring to FIG. 5, a block diagram of another illustrative embodiment of a system for providing alerts in response detecting that a disposable absorbent garment has been insulted is shown as a system 500. As shown in FIG. 4, the system 400 includes the diagnostic sheet 110 of FIG. 1 that includes the RFID 120 and the one or more diagnostic elements 112, the interrogator device of FIG. 2, the electronic device 410 of FIG. 4, and a second diagnostic sheet 540. The second diagnostic sheet 540 includes one or more diagnostic elements 542 and an RFID 544. In an embodiment, the one or more diagnostic elements 542 may correspond to or be substantially identical the one or more diagnostic elements 112, and the RFID 544 is configured similarly to the RFID 120. In an additional or alternative embodiment, the one or more diagnostic elements 542 may be different from the one or more diagnostic elements 112. For example, the one or more diagnostic elements 112 may include at least one diagnostic elements associated with a diagnostic test that is not included in the one or more diagnostic elements 542. Including different diagnostic tests on different diagnostic sheets may be beneficial when different users of the diagnostic sheets 110 and 540 are suspected of having different conditions or to diagnose different conditions that the respective users are being monitored for.

As illustrated in FIG. 5, the interrogator device 210 may include a processor 510, a memory 520, and a transceiver 526. The processor 510 may be a general-purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the operations of the interrogator device 210, as described with reference to FIGS. 1-5. The memory 520 may include random access memory (RAM) devices, read only memory (ROM) devices, one or more hard disk drives (HDDs), flash memory devices, solid state drives (SSDs), erasable programmable read only memory (EPROM) devices, electrically erasable programmable read only memory (EEPROM) devices, magnetoresistive random access memory (MRAM) devices, optical memory devices, cache memory devices, other memory devices configured to store data in a persistent or non-persistent state, or a combination of different memory devices. The memory 520 may store instructions 522 that, when executed by the processor 510, cause the processor to perform the operations of the interrogator device 210, as described with reference to FIGS. 1-5.

In FIG. 5, the diagnostic sheet 110 is shown at a first time (e.g., T=X) and the diagnostic sheet is shown at a second time (e.g., T=Y). The first time and the second time correspond to times when the fluid has been wicked to the RFID 120 and the RFID 544, as indicated by the dashed line 220 and the dashed line 550, respectively. In an embodiment, the first time and the second time may be the same time (e.g., T=X=Y). In an additional or alternative embodiment, the first time and the second time may be different times (e.g., X≠Y). Because the RFID 120 and the RFID 544 are in the presence of the fluid at the first time and the second time, respectively, each of the RFIDs 120 and 544 are shown generating a backscatter signal. For example, the RFID 120 is generating a backscatter signal 222 to provide an indication to the interrogator device 210 that a first disposable absorbent garment (e.g., a disposable garment being used in conjunction with the diagnostic sheet 110) has been insulted and that the one or more diagnostic elements 112 are in the presence of the fluid and are providing accurate results for the corresponding one or more diagnostic tests. Additionally, the RFID 544 is generating a backscatter signal 546 to provide an indication to the interrogator device 210 that a second disposable absorbent garment (e.g., a disposable garment being used in conjunction with the diagnostic sheet 540) has been insulted and that the one or more diagnostic elements 542 are in the presence of the fluid and are providing accurate results for the corresponding one or more diagnostic tests.

In response to receiving or detecting the first indication (e.g., the backscatter signal 222), the interrogator device 210 may generate a first alert, shown in FIG. 5 as a notification 404, that indicates the fluid has been wicked to the one or more diagnostic elements 112 by the diagnostic sheet 110. The notification 404 may be provided to the electronic device 410 associated with a caregiver of the wearer of the first disposable garment. The notification 404 may also be provided via an audible and/or a visual alert, as explained above with reference to FIG. 4. In response to receiving or detecting the second indication (e.g., the backscatter signal 546), the interrogator device 210 may generate a second alert, shown in FIG. 5 as a notification 504, that indicates the fluid has been wicked to the one or more diagnostic elements 542 by the diagnostic sheet 540. The notification 504 may be provided to an electronic device associated with a caregiver of the wearer of the second disposable garment. In an embodiment, the electronic device associated with the caregiver of the wearer of the second disposable garment may be the same electronic device (e.g., the electronic device 410) as the electronic device associated with the caregiver of the wearer of the first disposable garment. The notification 504 may also be provided via an audible and/or a visual alert, as explained above with reference to FIG. 4.

The backscatter signal 222 and the backscatter signal 546 may be different, despite being generated based on a common interrogation signal (e.g., the interrogation signal 212). For example, the RFID 120 may be configured to modulate the demodulated signal generated based on the interrogation signal 212 using a first modulation scheme that alters the phase and/or frequency of the demodulated signal a first amount, and the RFID 544 may be configured to modulate the demodulated signal generated based on the interrogation signal 212 using a second modulation scheme that alters the phase and/or frequency of the demodulated signal a second amount. The interrogator device 210 may distinguish the backscatter signals 222 and 546 based on the first and second modulation schemes.

In an embodiment, the first and second modulation schemes utilized by the RFID 120 and the RFID 544 may be statically configured. For example, a manufacturer of the diagnostic sheet 110 and the diagnostic sheet 540 may manufacturer diagnostic sheets including RFIDs having a plurality of different modulation schemes. The manufacturer may package the diagnostic sheets such that each package of diagnostic sheets includes only diagnostic sheets sharing a common modulation scheme. The different modulation schemes may be indicated on the packaging using a numeric identifier (or another type of identifier) representative of the particular modulation utilized by the RFIDs included in the package.

A consumer may or may not require different modulation schemes. For example, a parent having only one child may not need to utilize different modulation schemes, and thus, any package of diagnostic sheets could be used, because there will never be more than one wearer of disposable absorbent garments at a time. However, a parent having two or more children that use disposable absorbent garments may utilize the different modulation schemes to distinguish between which children need to be changed. For example, the interrogator device may be programmed with configuration information 524 that may be stored in the memory 520. The configuration information 524 may include information that indicates a number of diagnostic sheets that are to be used simultaneously by different wearers. The configuration information 524 may store information indicating that diagnostic sheets utilizing two different modulation schemes are to be used. In an embodiment, the names of the children may be entered into the configuration information 524, and each of the children may be associated with a particular numeric identifier indicating the modulation scheme corresponding to the diagnostic sheets that will be inserted into the children's disposable absorbent garments. For example, a first child may be associated with a first numeric identifier and a second child may be associated with a second identifier.

When changing the children's disposable absorbent garments, the parents (or a caregiver) may insert the appropriate diagnostic sheet (e.g., a diagnostic sheet having a numeric identifier corresponding to the identifier stored in the configuration information) into the child's disposable absorbent garments. Additionally, because the configuration information 524 knows the numeric identifier associated with the respective RFIDs, the interrogator device may be operable to distinguish the backscatter signals (e.g., the backscatter signals 222 and 546) generated using the different modulation schemes, and to provide targeted notifications specific to each child. For example, the notification may indicate that a first child has insulted his or her disposable absorbent garment. Thus, the caregiver does not need to check both children to see which child the notification pertains to. The ability to program the interrogator device 210 to distinguish between the backscatter signals of different diagnostic sheets may provide a greater advantage in a hospital, a daycare, a nursing home, or an assisted living setting, where there may be tens or hundreds of persons using disposable absorbable garments, and that require assistance from a caregiver or a medical professional.

In an embodiment, when the interrogator device 210 includes a camera, as described with reference to FIG. 4, the interrogator device 210 may be configured to provide the images of the one or more diagnostic elements of the respective diagnostic sheets to a medical professional or other healthcare provider. The configuration information 524 may store information (e.g., an e-mail address, a telephone number, a website, etc.) that may be used to provide the images to the medical professional or other healthcare provider. For example, the user of the interrogator device 210 may enter the information associated with the medical professional or other healthcare provider into the configuration information 524. Upon a user taking an image of one or more diagnostic elements, the interrogator device 210 may automatically transmit the image to the medical professional or other healthcare provider using the configuration information 524. In a hospital setting, this may be beneficial for quickly alerting medical staff to conditions such as dehydration.

In addition to storing images and the configuration information 524, the interrogator device 210 may track other information that may be provided to the medical professional, other healthcare provider, caregiver, or parent. For example, the interrogator device may be configured to store information descriptive of a number of times during a time period (e.g., one day) that a particular wearer of disposable absorbent garments insulted a disposable absorbent garment, a frequency at which the particular wearer insulted the disposable absorbent garments, or other information.

In an embodiment, the interrogator device may include a display (not shown in FIG. 5) that may be used to provide information to the interrogator device 210. For example, the instructions 522 may include instructions that, when executed by the processor 510, cause the processor 510 to present a graphical user interface at the display, and the graphical user interface may be used to program or enter information into the interrogator device 210. In an additional or alternative embodiment, the interrogator device 210 may include an interface (e.g., a universal serial bus (USB) interface) that enables the user of the interrogator device 210 to couple the interrogator device 210 to a computer, and the computer (or an application running on the computer) may be used to program or enter the information into the interrogator device 210. In an embodiment, an application executing on the electronic device 410 may enable the user of the electronic device 410 to view and/or modify the information (e.g., view a report regarding the number of times a wearer insulted a disposable absorbent garment during a time period, a report indicating a frequency at which the wearer insulted a disposable absorbent garment during a time period, the images of the one or more diagnostic elements captured using the interrogator device 210, or other information).

Figure 6:
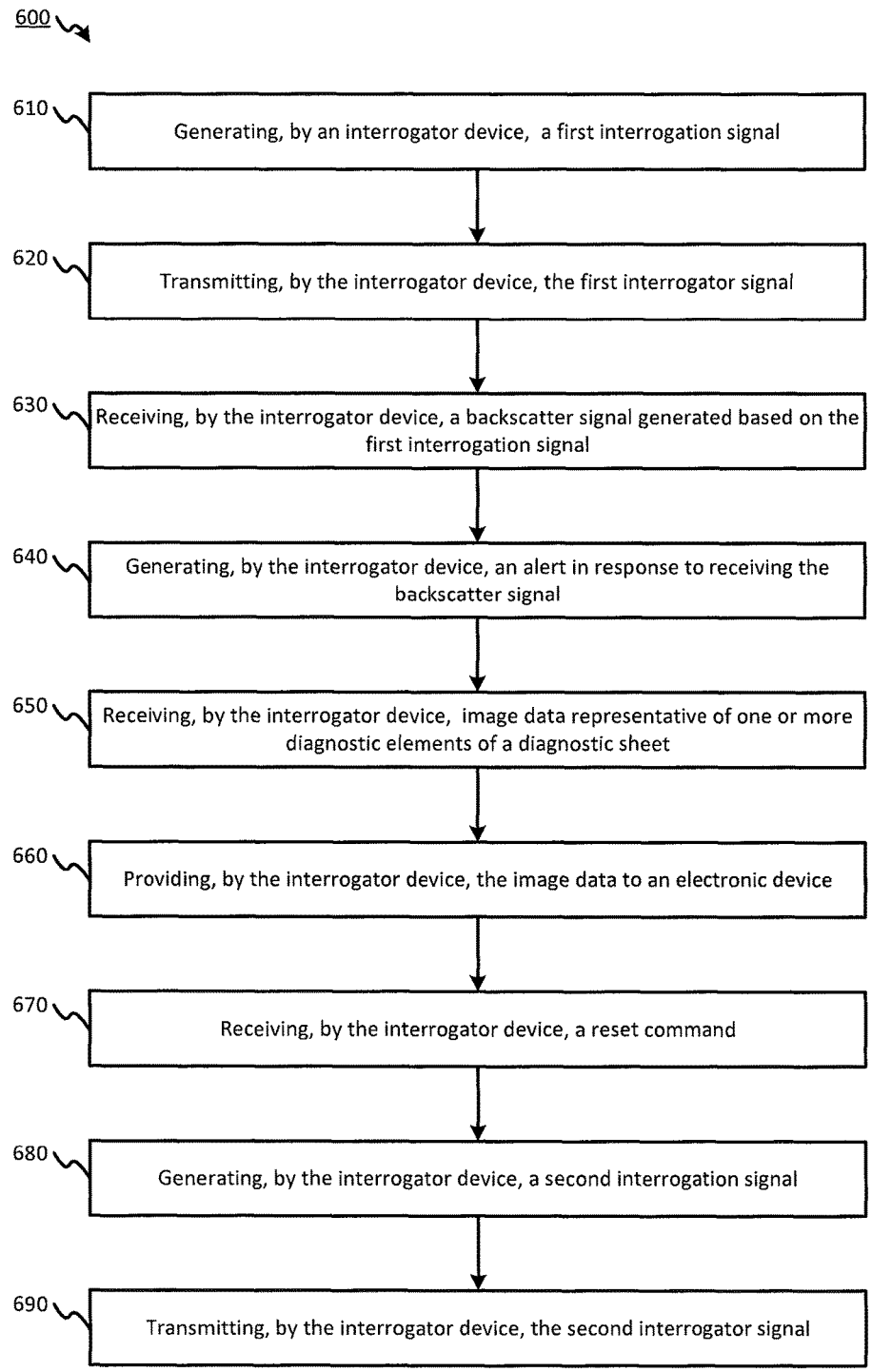
FIG. 6 is a flowchart illustrating an embodiment of a method for generating interrogation signals and alerts for use in conjunction with a diagnostic sheet and disposable absorbent garment.

Referring to FIG. 6, a flowchart illustrating an embodiment of a method for generating interrogation signals and alerts for use in conjunction with a diagnostic sheet and disposable absorbent garment is shown as a method 600. In an embodiment, the method 600 may be performed by the interrogator device 210 of FIGS. 2-5 and/or the interrogator device described with reference to FIG. 1. In an embodiment, the method 600 may be stored as instructions (e.g., instructions 522 of FIG. 5) that, when executed by a processor (e.g., the processor 510 of FIG. 5), cause the processor to perform operations corresponding to the method 600.

At 610, the method 600 includes generating, by an interrogator device, a first interrogation signal, and, at 620, transmitting, by the interrogator device, the first interrogation signal. In an embodiment, the interrogation signal may be the interrogation signal 212 of FIGS. 2-5. At 630, the method 600 includes receiving, by the interrogator device, a backscatter signal generated based on the first interrogation signal. For example, the backscatter signal may be generated by a passive RFID (e.g., the RFID 120 of FIGS. 1-5) that demodulates the first interrogation signal and then performs modulation of the demodulated first interrogation signal to generate the backscatter signal, as described with reference to FIG. 1. At 640, the method 600 includes generating, by the interrogator device, an alert in response to receiving the backscatter signal. The alert may be an audible or visual alert, as described with reference to FIGS. 4 and 5, and/or another form of alert, such as a text message, an automated voice messaging system message, or some other alert mechanism, as described with reference to FIGS. 4 and 5.

At 650, the method 600 includes receiving, by the interrogator device, image data representative of one or more diagnostic elements of a diagnostic sheet. In an embodiment, the image data may be captured by an imaging device integrated with the interrogator device, as described with reference to FIGS. 4 and 5, or may be received from another device (e.g., a computer, a wireless communication device, etc.). The diagnostic sheet may be the diagnostic sheet 110 of FIGS. 1-5, and the one or more diagnostic elements may be the one or more diagnostic elements 112 of FIGS. 1-5. At 660, the method 600 includes providing, by the interrogator device, the image data to an electronic device. In an embodiment, the electronic device and/or an address associated with the electronic device may be determined based on configuration information, such as the configuration information 524 of FIG. 5.

In an embodiment, the method 600 may include receiving additional backscatter signals generated based on the first interrogation signal. For example, additional RFID devices integrated with additional diagnostic sheets may receive the first interrogation signal, and, if in the presence of a fluid, may generate the additional backscatter signals, as described with reference to FIG. 5. Each of the additional backscatter signals may be unique or otherwise distinguishable at the interrogator device, and the interrogator device may be configured to generate additional alerts based on the configuration information and the additional backscatter signals, as described with reference to FIG. 5.

At 670, the method 600 includes receiving, by the interrogator device, a reset command. For example, the interrogator device may include a reset button, as described with reference to FIGS. 4 and 5, that may be pressed when a caregiver changes a disposable absorbent garment that has been insulted. At 680, the method 600 includes generating, by the interrogator device, a second interrogation signal in response to receiving the reset command, and, at 690, transmitting, by the interrogator device, the second interrogation signal. The second interrogation signal may allow the interrogator device to distinguish between notifications (e.g., backscatter signals) for which alerts were previously generated and notifications for which alerts need to be generated (e.g., alters for notifications generated using a currently transmitted interrogation signal), as described with reference to FIGS. 4 and 5.

As explained with reference to FIGS. 4 and 5, an interrogator device according to one or more of the embodiment disclosed herein may provide advantages to healthcare providers and caregivers. For example, the ability to generate and transmit multiple interrogation signals may help prevent false alerts (e.g., alerts for backscatter signals received from disposable absorbent garments and RFIDs that have been changed), and may help provide more intelligent alerts (e.g., alerts that are specific to a particular one of a plurality of wearers of disposable absorbent garments), as described with reference to FIGS. 4 and 5. Additionally, the ability to capture images using the interrogator device and to provide the images from the interrogator device to another electronic device (e.g., a device associated with a healthcare provider) may make a system, such as the systems described with reference to FIGS. 2-5 that incorporated RFIDs and diagnostic elements into disposable absorbent garments more easy to use.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. An article for use in conjunction with a disposable absorbent garment, the article comprising:
    a diagnostic sheet operable to wick fluid vertically, the diagnostic sheet including:
        one or more diagnostic elements integrated with the diagnostic sheet and positioned at a first region of the diagnostic sheet; and
        a radio frequency identification device (RFID) integrated with the diagnostic sheet and positioned proximate the first region of the diagnostic sheet, wherein the RFID includes:
            an antenna configured to receive and transmit signals;
            signal generation circuitry configured to generate a signal for transmission by the antenna based on a wireless signal received at the antenna from an interrogator device;
            power generation circuitry configured to provide operational power to the signal generation circuitry based on the wireless signal received at the antenna from the interrogator device; and
            power control circuitry configured to disable the provisioning of power, by the power generation circuitry, to at least the signal generation circuitry until at least a portion of the power control circuitry is in the presence of the fluid,
        wherein, in the presence of the fluid wicked to one or more diagnostic elements by the diagnostic sheet, each of the one or more diagnostic elements is configured to indicate a result of a particular diagnostic test, and
        wherein the signal generated by the signal generation circuitry is configured to provide an indication to the interrogator device that the fluid has been wicked to the one or more diagnostic elements by the diagnostic sheet, the indication configured to cause the interrogator device, in response to receiving the signal, to generate a notification that indicates the fluid has been wicked to the one or more diagnostic elements by the diagnostic sheet.

2. The article of claim 1, wherein each of the one or more diagnostic elements is selected from the list consisting of: a pH test, a specific gravity test, a protein test, a blood test, a glucose test, a ketone test, a bilirubin test, a urobilinogen test, a nitrites test, and a leukocytes test.

3. The article of claim 1, wherein the article is integrated into a disposable absorbent garment as a top sheet.

4. The article of claim 1, wherein the diagnostic sheet includes a front edge, wherein first region is proximate a front edge of the diagnostic sheet, and wherein the RFID is positioned between the one or more diagnostic elements and the front edge of the diagnostic sheet.

5. A disposable absorbent garment comprising:
    a backsheet;
    an absorbent core; and
    a top sheet configured to wick fluid, the top sheet including:
        one or more diagnostic elements integrated with the top sheet and positioned at a first region of the top sheet, wherein each of the one or more diagnostic elements is configured to, in the presence of the fluid wicked to one or more diagnostic elements by the top sheet, indicate a result of a particular diagnostic test; and
        a radio frequency identification device (RFID) integrated with the top sheet and positioned proximate the first region of the top sheet, wherein, in the presence of the fluid wicked to the RFID by the top sheet, the RFID is configured to provide an indication that the fluid wicked by the top sheet has reached the one or more diagnostic element, and wherein the RFID includes:
            an antenna; and
            circuitry configured to:
                power the RFID device in response to receiving a wireless signal from an interrogator device at the antenna,
                generate a signal based on the received signal, and
                provide the signal to the antenna for transmission,
            wherein the circuitry is configured to cease providing power to the RFID device and to cease providing the signal when the wireless signal is received from the interrogator device and at least a portion of the circuitry is in the presence of the fluid wicked to the RFID by the top sheet, and
            wherein the indication is provided by ceasing transmission of the signal, and
            wherein the indication is configured to, when detected by an interrogator device, cause the interrogator device to generate a notification that indicates the fluid has been wicked to the one or more diagnostic elements by the top sheet; and
    an intermediate top sheet disposed between the top sheet and the absorbent core;
    wherein the absorbent core is disposed between the backsheet and the intermediate top sheet.

6. The disposable absorbent garment of claim 5, wherein each of the one or more diagnostic elements is selected from the list consisting of: a pH test, a specific gravity test, a protein test, a blood test, a glucose test, a ketone test, a bilirubin test, a urobilinogen test, a nitrites test, and a leukocytes test.

7. The disposable absorbent garment of claim 5, wherein the top sheet that includes the one or more diagnostic elements and the RFID, and wherein the top sheet is removable.

8. The disposable absorbent garment of claim 5, wherein the top sheet includes a back edge and a front edge, wherein first region is proximate the front edge, and wherein the RFID is positioned between the one or more diagnostic elements and the front edge.

9. The disposable absorbent garment of claim 5, wherein the top sheet includes a back edge and a front edge, wherein first region is proximate the back edge, and wherein the RFID is positioned between the one or more diagnostic elements and the back edge.

10. A system comprising:
    a diagnostic sheet configured to wick fluid vertically, wherein the diagnostic sheet includes:
        one or more diagnostic elements integrated with the diagnostic sheet and positioned at a first region of the diagnostic sheet, wherein each of the one or more diagnostic elements is configured to, in the presence of the fluid wicked to one or more diagnostic elements by the diagnostic sheet, indicate a result of a particular diagnostic test;
        a radio frequency identification device (RFID) integrated with the diagnostic sheet and positioned proximate the first region of the diagnostic sheet, wherein the RFID includes:

an antenna configured to receive and transmit signals;

signal generation circuitry configured to generate a signal for transmission by the antenna based on a wireless signal;

power generation circuitry configured to provide operational power to the signal generation circuitry based on the wireless signal received at the antenna; and power control circuitry configured to disable the provisioning of power, by the power generation circuitry, to at least the signal generation circuitry until at least a portion of the power control circuitry is in the presence of the fluid; and an interrogator device configured to:

transmit the wireless signal;

receive the signal generated by the signal generation circuitry; and generate a notification that indicates the fluid has been wicked to the one or more diagnostic elements by the diagnostic sheet in response to receiving the signal generated by the signal generation circuitry.

11. The system of claim 10, wherein the diagnostic sheet has a hydrophilic non-woven structure.

12. The system of claim 10, wherein the notification generated by the interrogator device includes one or more of a text message, an audible alert, an automated voice messaging system message, a visual alert.

13. The system of claim 10, further comprising a second diagnostic sheet configured to wick fluid vertically, wherein the second diagnostic sheet includes:

one or more second diagnostic elements positioned at a first region of the second diagnostic sheet, wherein each of the one or more second diagnostic elements is configured to indicate a result of a particular diagnostic test in the presence of the fluid wicked to the one or more second diagnostic elements by the second diagnostic sheet; and a second RFID integrated with the second diagnostic sheet and positioned proximate the first region of the second diagnostic sheet, wherein the second RFID includes:

an antenna configured to receive and transmit signals;

signal generation circuitry configured to generate a signal for transmission by the antenna based on a wireless signal;

power generation circuitry configured to provide operational power to the signal generation circuitry based on the wireless signal received at the antenna from the interrogator device; and a power control circuit configured to disable the provisioning of power, by the power generation circuitry, to at least the signal generation circuitry until at least a portion of the power control circuit is in the presence of the fluid.

14. The system of claim 13, wherein the interrogator device is configured to:

receive the signal generated by the signal generation circuitry of the second RFID; and generate a second notification that indicates the fluid has been wicked to the one or more second diagnostic elements by the second diagnostic sheet in response to receiving the signal generated by the signal generation circuitry of the second RFID.

15. The system of claim 14, wherein the second notification generated by the interrogator device includes one or more of a text message, an audible alert, an automated voice messaging system message, a visual alert, and wherein the second notification is different than the notification.

16. The system of claim 10, wherein the diagnostic sheet includes one or more perforations for resizing the diagnostic sheet.

17. The system of claim 13, wherein the diagnostic sheet is associated with a first disposable absorbent garment worn by a first user and the second diagnostic sheet is associated with a second disposable absorbent garment worn by a second user.

* * * * *